United States Patent [19]

Richards et al.

[11] Patent Number: 4,669,473
[45] Date of Patent: Jun. 2, 1987

[54] SURGICAL FASTENER

[75] Inventors: William D. Richards, Medway; Philip R. Lichtman, Newton, both of Mass.

[73] Assignee: Acufex Microsurgical, Inc., Norwood, Mass.

[21] Appl. No.: 773,355

[22] Filed: Sep. 6, 1985

[51] Int. Cl.[4] ............... A61B 17/04; A61B 17/08
[52] U.S. Cl. ................... 128/334 C; 128/335
[58] Field of Search ............ 128/334 R, 335, 334 C, 128/337; 227/67; 24/150 P, 150 FP, 90 R; 112/104 R; 411/458, 459, 460, 457, 446, 447

[56] References Cited

U.S. PATENT DOCUMENTS

| | | | |
|---|---|---|---|
| 2,901,796 | 9/1957 | Hope | 24/90 R |
| 3,028,646 | 11/1959 | Janes | 24/90 R |
| 3,103,666 | 12/1961 | Bone | 227/67 |
| 3,399,432 | 4/1967 | Merser | 24/150 FP |
| 3,470,834 | 3/1968 | Bone | 227/67 |
| 3,494,004 | 3/1968 | Bone | 24/90 R |
| 3,875,648 | 9/1975 | Bone | 29/417 |
| 3,931,667 | 1/1976 | Merser et al. | 24/150 P |
| 3,973,299 | 8/1976 | Keefe | 24/150 FP |
| 3,979,799 | 9/1976 | Merser et al. | 24/150 P |
| 3,990,619 | 11/1976 | Russell | 227/67 |
| 4,006,747 | 2/1977 | Knonethal | 128/335 |
| 4,039,078 | 8/1977 | Bone | 227/67 |
| 4,121,487 | 10/1978 | Bone | 227/67 |
| 4,235,238 | 11/1980 | Ogiu et al. | 128/335 |
| 4,454,875 | 6/1984 | Pratt et al. | 128/334 R |

FOREIGN PATENT DOCUMENTS

| | | | |
|---|---|---|---|
| 129442 | 12/1984 | European Pat. Off. | 128/334 C |
| 284898 | 3/1928 | United Kingdom | 411/460 |

Primary Examiner—Richard C. Pinkham
Assistant Examiner—Gary Jackson
Attorney, Agent, or Firm—Schiller, Pandiscio & Kusmer

[57] ABSTRACT

An improved surgical fastener having at least one head portion and a filament portion arranged in a T configuration, wherein at least one end of the said at least one head portion is sharply pointed, so that when that head portion is implanted in body tissue, the head portion will attach itself securely to the tissue and will remain there despite the application of a substantial pulling force on the filament portion.

37 Claims, 17 Drawing Figures

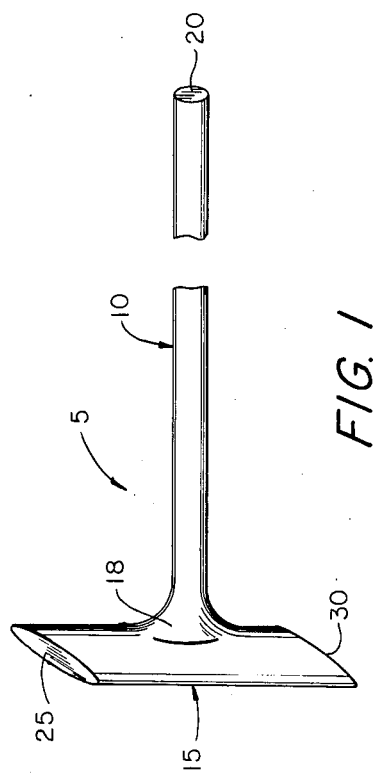
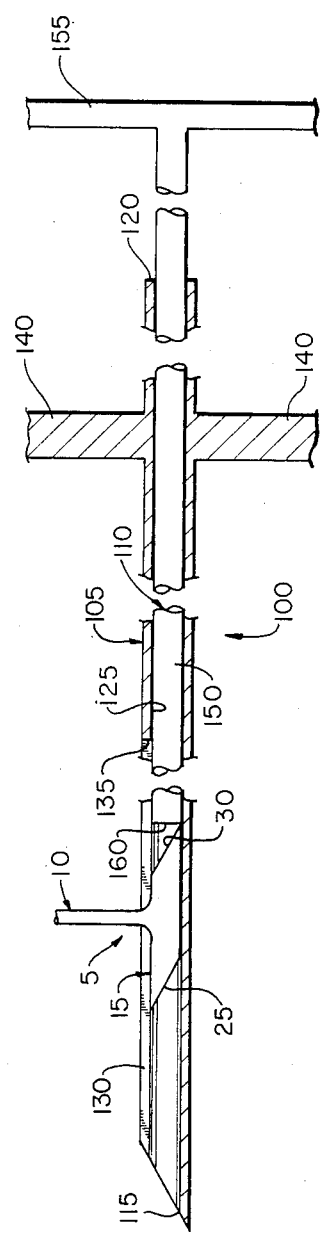
FIG. 1
FIG. 2

SURGICAL FASTENER

FIELD OF THE INVENTION

This invention relates to surgical apparatus in general, and more particularly to surgical fasteners of the sort used to effect surgical attachments.

BACKGROUND OF THE INVENTION

The conventional method for effecting surgical attachments involves the time-honored technique of sewing with needle and suture. Over the years a wide variety of needle sizes and shapes and suture sizes and compositions have been developed to meet the demands of many different suturing situations. More recently, other methods and means have been developed as an alternative to conventional suturing. For example, a great deal of work has been done in the area of surgical stapling.

In U.S. Pat. Nos. 4,006,747 and 4,235,238, surgical fasteners are disclosed which can be used to attach two or more tissue members to one another, e.g. so as to close a surgical incision. These surgical fasteners generally comprise a relatively short, flexible filament having a relatively rigid, bar-like head on each end thereof, wherein the bar-like head normally resides perpendicular to the adjoining length of filament during use. These surgical fasteners, sometimes referred to as "T-bar" fasteners due to their shape, are deployed using a special tool which, in cooperation with the tissue members being joined, causes one of the fastener's heads and the adjoining length of filament to be temporarily aligned with one another, whereby that head and the filament can be threaded through the two or more tissue members which are being joined. The several tissue members are then captivated on the filament between the fastener's two bar-like heads.

In certain circumstances it may be desirable to have the surgical fasteners disposed so that at least one end thereof is anchored inside body tissue, rather than simply bearing inwardly against the outer surface of the body tissue as with the T-bar fasteners described above. See, for example, U.S. Pat. No. 3,716,058, which discloses a short section of suture material having a return barb on each end. Some attention has been directed towards utilizing T-bar fasteners in a similar manner. For example, T-bar fasteners have been used for attaching informational tags to meat, wherein one end of the T-bar fastener is anchored inside the meat while the other end is allowed to dangle free outside the meat, with the tag attached. In this respect it should be noted, however, that all of the T-bar fasteners known to date comprise arrangements wherein the end surfaces of the fastener's bar-like heads are formed either flat (see, for example, U.S. Pat. Nos. 2,069,878, 3,990,619, 4,006,747, 4,039,078 and 4,235,238) or effectively rounded (see, for example, U.S. Pat. Nos. 3,103,666, 3,399,432, 3,470,834, 3,494,004, 3,931,667 and 3,979,799). As a result, the holding power of the T-bar fasteners is quite limited. In the meat tagging application described above, the limited holding power provided by the flat or effectively rounded end surfaces of the fastener heads is not only tolerable but actually desirable, since it allows the fasteners to be easily pulled out of the meat upon the application of a moderate pulling force, e.g., when the meat is being prepared for cooking.

However, such a construction is clearly not acceptable in the case of surgical applications where it may be critical that the T-bar fasteners remain solidly anchored in the body tissue despite the application of a substantial pulling force.

OBJECTS OF THE INVENTION

Accordingly, the principal object of the present invention is to provide an improved surgical fastener of the T-bar variety arranged so that when at least one T-bar end thereof is deployed inside body tissue, that end of the fastener will remain solidly anchored in the tissue despite the application of a substantial pulling force.

Another object is to provide an improved surgical fastener which is simple and inexpensive to make, easy to use, and adapted to being reliably anchored in living tissue.

Still another object is to provide an improved surgical fastener of the T-bar variety which can be made either absorbable or non-absorbable to the human body.

SUMMARY OF THE INVENTION

These and other objects of the invention are achieved by providing a novel surgical fastener comprising a filament and at least one bar-like head, with the filament being resilient and relatively flexible along its length and the at least one bar-like head being relatively inflexible along its length and attached to the filament so that it normally resides perpendicular to the adjoining length of filament, and further wherein at least one end of the at least one bar-like head has at least one sharp point which promotes anchoring of the head in tissue. When that head of the fastener is driven into body tissue so that the filament extends along the axis of driving, the natural resiliency of the fastener will cause the sharp point to embed itself in the tissue in a manner which securely anchors the T-bar head so that it may not be easily withdrawn from the tissue when the filament is subjected to a pulling force.

BRIEF DESCRIPTION OF THE DRAWINGS

These and other objects and features of the present invention are described in or rendered obvious by the following detailed description of the preferred embodiment of the invention, which is to be considered together with the accompanying drawings wherein like numbers refer to like parts and further wherein:

FIG. 1 is a perspective view illustrating a first preferred form of surgical fastener made in accordance with the present invention;

FIG. 2 is a longitudinal sectional view of a tool for deploying the surgical fastener shown in FIG. 1;

DETAILED DESCRIPTION OF THE PREFERRED EMBODIMENT

Figure 3:
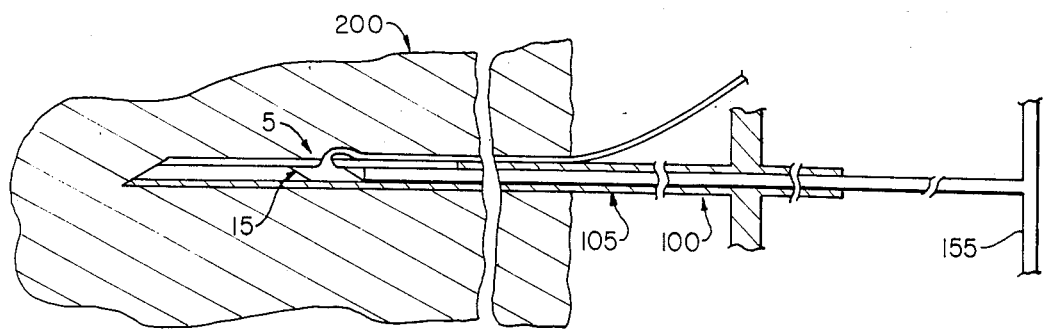
FIGS. 3-5 are sectional views in side elevation illustrating how the tool of FIG. 2 is used to deploy the surgical fastener of FIG. 1 in body tissue.

Looking first to FIG. 1, there is shown a one-piece surgical fastener 5 which comprises a relatively long thin filament 10. One end of filament 10 terminates in a relatively short, thick bar-like head 15 that has a round cross-section, while the other end of filament 10 terminates in a surface 20 that may be flat or rounded. Filament 10 necks outward at its base 18 where it joins head 15. Head 15 is integral with filament 10 and the fastener is formed so that head 15 normally extends at a right angle to the adjoining length of filament. One end of the bar-like head 15 terminates in a flat surface 25, and the other end of head 15 terminates in a flat surface 30. Surfaces 25 and 30 are set at an inclined angle (approximately 30-45 degrees) relative to the longitudinal axis of head 15, whereby head 15 is sharply pointed at each end with the sharp points being eccentric, i.e., radially displaced, from the longitudinal axis of head 15.

T-bar fastener 5 is formed out of a resilient polymerized resin, with the relatively thin filament 10 being relatively flexible along its length and the relatively thick bar-like head 15 being relatively stiff along its length, in accordance with the teachings of U.S. Pat. No. 4,121,487 and the references cited therein. For example, in the situation where fastener 5 is to be made absorbable to the body, the fastener may be formed out of a polylactide copolymer or a glycolide copolymer (see U.S. Pat. Nos. 3,636,956 and 4,300,565), and in the situation where fastener 5 is to be made non-absorbable to the body, the fastener may be formed out of a suitable nylon or polyethylene or carbonate polymer or polyether ester copolymer (see U.S. Pat. Nos. 4,300,565 and 4,314,561). While the precise dimensions of fastener 5 will vary according to the specific surgical application, for many applications it is acceptable or even preferred to make fastener 5 so that filament 10 has a diameter of 0.015 inches and head 15 has a diameter of 0.030 inches and a length of 0.180 inches. It is preferred that the length of head 15 be between about 0.165 inches and 0.195 inches. The length of filament 10 is not critical but should be long enough for its free end to protrude from the outer surface of the tissue in which it is implanted by a distance suitable for the needs of the surgeon.

FIG. 2 illustrates a tool 100 for deploying fastener 5. Tool 100 generally comprises a hollow sheath or needle 105 and a plunger or ram 110. Sheath 105 terminates in a flat annular surface 115 at its front end and a flat annular surface 120 at its rear end. Front surface 115 is disposed at an inclined angle (approximately 30 degrees) relative to the longitudinal axis of sheath 105, so that the sheath is effectively sharply pointed at its front end. Rear surface 120 is disposed at an angle substantially perpendicular to the longitudinal axis of sheath 105. Sheath 105 has an axial bore 125 extending between its front surface 115 and its rear surface 120, and a straight slot 130 extending rearwardly from the tool's front surface 115 and terminating in a rear surface 135. Sheath 105 also includes a pair of rigid finger grips 140 which extend radially outward from the sheath near its rear surface 120. Plunger 110 is a one-piece unit and includes a body section 150 and a head section 155. Body section 150 has a round cross-section and terminates in a front surface 160. Plunger 110 is sized so that body section 150 will make a close sliding fit within bore 125 of sheath 105, and so that its leading tip 160 will protrude from the front end of the sheath a short distance when the plunger's head section 155 is in engagement with the sheath's rear surface 120 (see FIG. 4).

Tool 100 is adapted to receive a fastener 5 in the manner shown in FIG. 2, i.e., the bar-like head 15 of the fastener is positioned inside bore 125 of sheath 105, with end surface 25 leading and end surface 30 trailing, while the filament 10 extends out through slot 130. Fastener 5 and tool 100 are carefully sized relative to one another so that head 15 will make a close sliding fit within the sheath, whereby head 15 may be easily loaded into the sheath but is capable of only minimal lateral movement within the sheath. It is to be appreciated that the width of the sheath's slot 130 is larger than the diameter of filament 10 but smaller than the diameter of head 15, in order to allow the filament to move freely lengthwise of the slot and to prevent head 15 from leaving bore 125 through slot 130.

Once fastener 5 has been loaded in tool 100 in the foregoing manner, the tool is ready to implant the fastener into body tissue. Looking next at FIG. 3, the fastener is deployed by pushing tool 100 pointed tip first into a piece of body tissue 200 while the plunger is retained in retracted position. Head 15 of fastener 5 is carried inside the body tissue by the tool. As this occurs, the fastener's filament is bent through interaction with the surrounding tissue so as to extend along the side of sheath 105, with the free end 20 of the filament residing outside the tissue.

Figure 4:
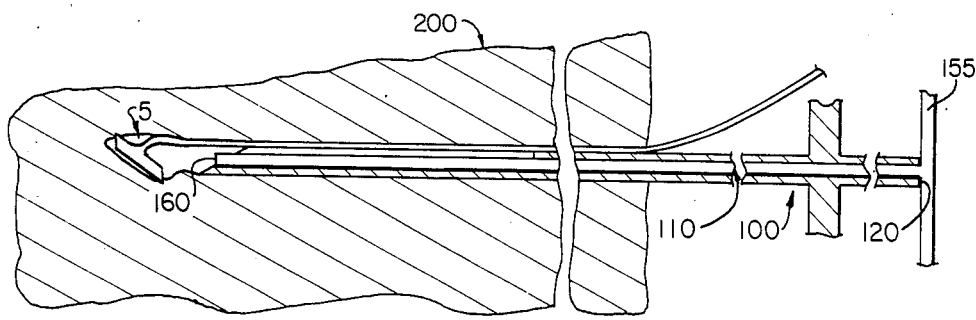

Looking next at FIG. 4, as soon as the pointed tip of sheath 105 has penetrated the tissue to a suitable depth, the head of the fastener is ejected from the tool and deployed into the body tissue by pushing plunger 110 forward until the plunger's head section 155 engages the rear surface 120 of the sheath. As this occurs, the leading end 160 of the plunger engages the rearmost portion of the head 15 and propels the fastener head forward out of the sheath and into tissue 200. Tool 100 typically retreats slightly under this action, leaving an opening in the tissue to accomodate the fastener's head. The resilient nature of the fastener thereupon causes the fastener to try to straighten on itself, i.e., to cause head 15 to assume its original right angle position relative to filament 10. This straightening or restoring action causes the sharply pointed ends of the fastener's head to dig into the surrounding tissue as the head turns in its attempt to resume its normal position substantially perpendicular to the adjoining length of filament of the fastener. Due to the fact that the hole formed in the tissue by the retreating tool 100 is significantly smaller in diameter than the length of fastener head 15, and also to the fact that the hole will tend to close inwardly somewhat under the pressure of the surrounding tissue, the fastener's head will typically be able to return only a fraction of the way back to its original perpendicular position; however, the sharply pointed ends of the fastener's head will nonetheless cause the fastener to penetrate sufficiently into the walls of the tissue so that the fastener will be anchored to the body tissue.

It is an important feature of the present invention that the sharply pointed ends of the fastener's head be formed in such a way, and presented to the tissue in such a way, that they will be able to engage the tissue and anchor the fastener in the manner just described. Thus, the fasteners have their pointed ends formed by terminating the ends of the head with a single planar surface 25 (or 30) set at an acute angle relative to the longitudinal axis of the head, whereby the two points are directed away from one another. In this preferred embodiment, bevelled end surfaces are arranged so that one of the points is positioned on the "filament" side of the head and the second point is positioned on the "outside" side of the head, i.e., displaced 180 degrees from the first point. This arrangement contrasts sharply with a conventional conical point where the point is on the axis of the bar-like head. Furthermore, the fastener is carefully positioned within sheath 105 so that the fastener's end surface 25 is leading and end surface 30 is trailing. As a result, when the head of the fastener is ejected from tool 100, the leading point, provided by end surface 25, is ready to pivot upward (clockwise in FIG. 2) and directly engage the tissue while the point provided by end surface 30 is ready to pivot downward (also clockwise in FIG. 2) and directly engage the tissue, without any other portion of the fastener engaging the tissue first to thereby deflect the turning and anchoring action of the fastener head. It is to be appreciated that if fastener 5 were loaded in tool 100 with end surface 30 leading and end surface 25 trailing, the fastener might very well fail to set itself properly into the wall of the tissue.

Figure 5:
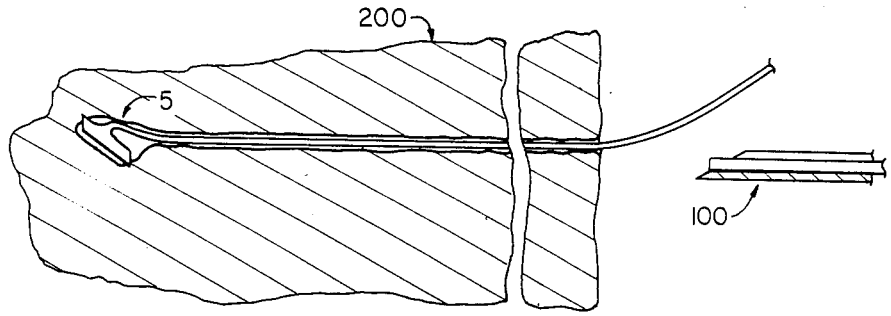

Thereafter tool 100 is withdrawn from tissue 200, leaving the fastener in the position shown in FIG. 5 whereby its head 15 is firmly emplanted in the body tissue while its filament 10 extends through the tissue to the region outside the tissue. If subsequently the free end of the fastener is pulled on, the fastener will not come free easily, due to the holding action provided by head 15. Indeed, on account of the angle at which the fastener's sharpened head is disposed in the tissue, pulling on the free end of the fastener tends to set the fastener ever deeper into the tissue.

Figure 6:
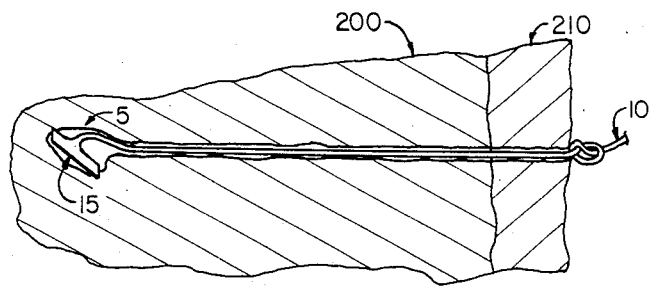
FIG. 6 is a sectional view in side elevation illustrating the surgical fastener of FIG. 1 attaching two different pieces of body tissue to one another.

The embedded fastener 5 may be used in ways well known in the art. For example, the fastener may have the free end of the filament attached to another tissue portion, e.g., by stitching, or it may thereafter be tied to the free end of another fastener which is itself similarly mounted to another tissue portion. As an alternative, the loose end of the filament of fastener 5 may simply be knotted if the fastener has already been attached to two tissue members, e.g. such as shown in FIG. 6, where fastener 5 is shown fastening together tissue portions 200 and 210.

Figure 7:
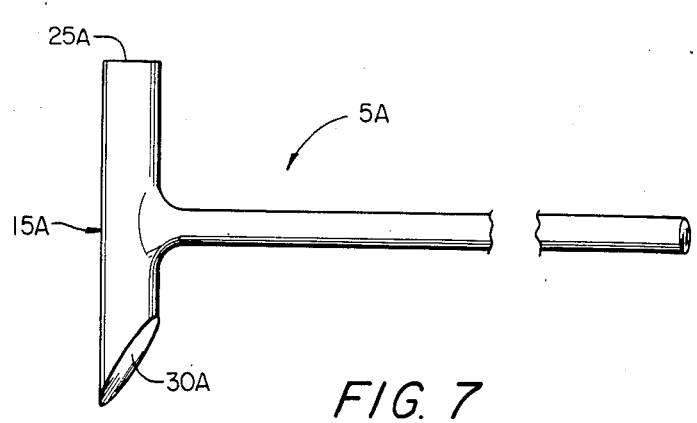
FIG. 7 is a perspective view illustrating a second form of surgical fastener made in accordance with the present invention.

Looking next at FIG. 7, there is shown a fastener 5A that is identical to the fastener 5 previously described, except that it has only one end of its bar-like head 15A sharply pointed. Thus while flat surface 30A of fastener 5A is set at an inclined angle relative to the longitudinal axis of head 15A, flat surface 25A is set at a right angle relative to the longitudinal axis of head 15A. Fastener 5A is positioned in tool 100 in substantially the same manner as fastener 5, i.e., with end surface 25A leading and end surface 30A trailing. Retention of fastener 5A is achieved by engagement of the point formed by flat surface 30A with the adjacent portion of the surrounding tissue.

Figure 8:
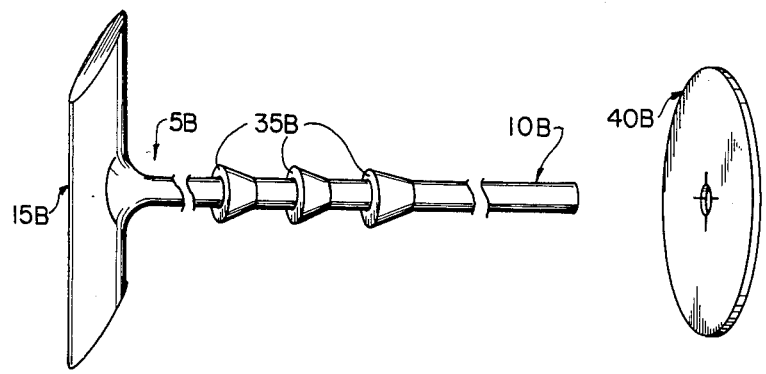
FIG. 8 is a perspective view illustrating a third form of surgical fastener made in accordance with the present invention.
Figure 9:
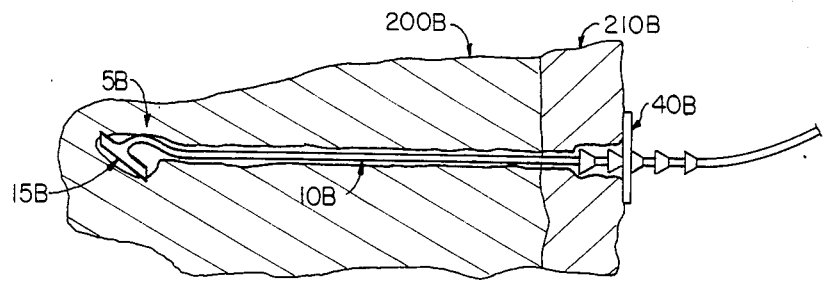
FIG. 9 is a sectional view in side elevation illustrating the surgical fastener of FIG. 8 attaching two different pieces of body tissue to one another.

Looking next at FIG. 8, there is shown a fastener 5B that is identical to the fastener 5 previously described, except that fastener 5B is provided with a plurality of ribs 35B along its filament 10B. Ribs 35B are conically shaped so as to allow an associated flexible washer 40B to be slid over the free end of filament 10B in the direction of head 15B, but to prevent return movement of the washer. Fastener 5B is useful for captivating two tissue sections against one another, wherein head 15B is embedded in the interior of one of the tissue sections and washer 40B bears against the outer surface of the other tissue section. This form of use is shown in FIG. 9, where fastener 5B and washer 40B are shown fastening together tissue section 200B and 210B.

Figure 10:
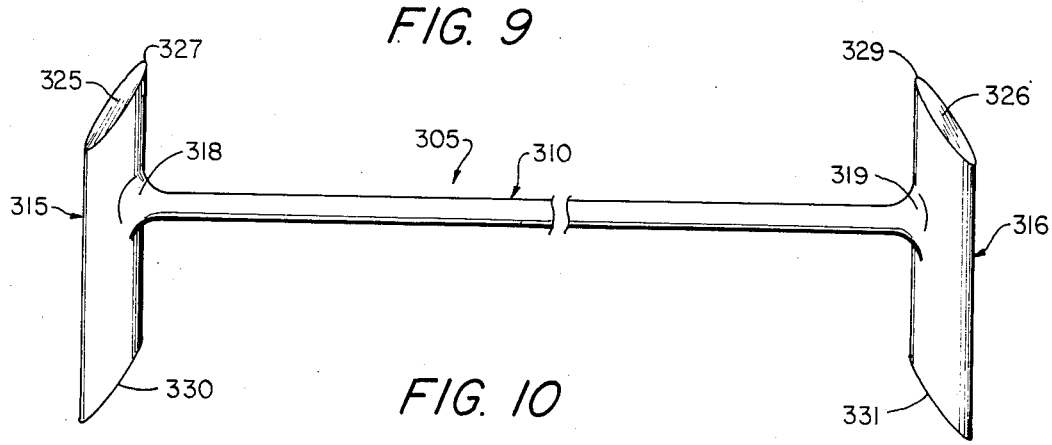
FIG. 10 is a perspective view illustrating a fourth form of surgical fastener made in accordance with the present invention.

Looking next at FIG. 10, there is shown a surgical fastener 305 which is simply two of the fasteners 5 of FIG. 1 joined together at their filament sections. More specifically, surgical fastener 305 comprises a relatively long thin filament 310 terminating at one end in a relatively short, thick bar-like head 315 and on the other end in a similar relatively short, thick bar-like head 316. Filament 310 necks outward at its bases 318 and 319 where it joins heads 315 and 316, respectively. Heads 315 and 316 are formed integral with filament 310 so that they normally extend at a right angle to the adjoining lengths of the filament. One end of bar-like head 315 terminates in a flat surface 325, and the other end of head 315 terminates in a flat surface 330. Similarly, one end of bar-like head 316 terminates in a flat surface 326, and the other end of head 316 terminates in a flat surface 331. Surfaces 325 and 330 are set at an inclined angle (approximately 30-45 degrees) relative to the longitudinal axis of head 315, and surfaces 326 and 331 are set at an inclined angle (approximately 30-45 degrees) relative to the longitudinal axis of head 316, whereby heads 315 and 316 are effectively sharply pointed at each end. It is to be appreciated, however, that, as shown in FIG. 10, surfaces 326 and 331 are pitched in a direction reversed to surfaces 325 and 330, respectively, for reasons which will hereinafter be made clear.

Fastener 305 is formed out of a resilient material such that its relatively thin filament 310 is relatively flexible along its length and the relatively thick bar-like heads 315 and 316 are relatively stiff along their length. For example, in the situation where fastener 305 is to be made absorbable to the body, the fastener may be formed out of a polylactide copolymer or a glycolide copolymer, and in the situation where fastener 305 is to be made non-absorbable to the body, the fastener may be formed out of a suitable nylon or polyethylene or carbonate copolymer or polyether ester copolymer. The two heads 315 and 316 and filament 310 have the same physical characteristics as the head 15 and filament 10 of fastener 5. Thus, while its dimensions may be varied according to the specific surgical application, for many applications it is acceptable or even preferred to make fastener 305 so that filament 310 has a diameter of 0.015 inches and heads 315 and 316 have diameters of 0.030 inches and lengths of 0.180 inches.

Figure 11:
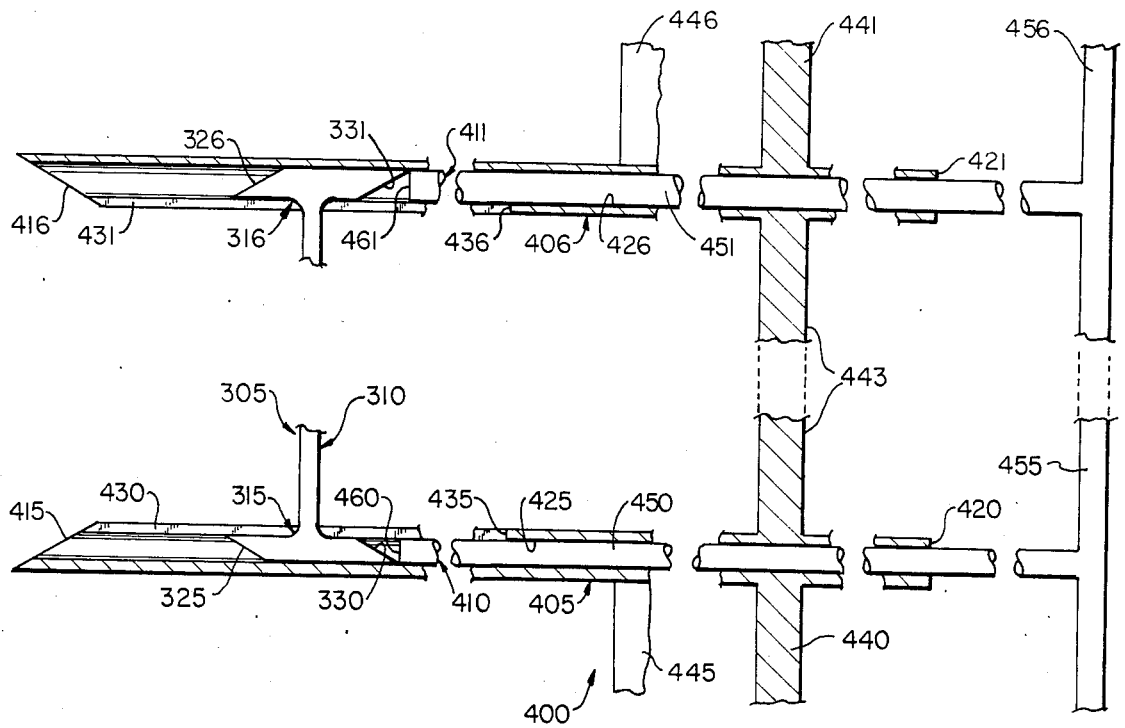
FIG. 11 is a longitudinal sectional view of a tool for deploying the surgical fastener shown in FIG. 10.

FIG. 11 shows a tool 400 for deploying fastener 305. Tool 400 may be considered as comprising two of the tools 100 of FIG. 2 joined together. More specifically, tool 400 comprises a pair of parallel hollow sheaths or needles 405 and 406 and a pair of plungers or rams 410 and 411.

Sheath 405 is a cylindrical tube that terminates in a flat annular surface 415 at its front end and a flat surface 420 at its rear end. Front surface 415 is disposed at an inclined angle (approximately 30 degrees) relative to the longitudinal axis of sheath 405, so that the sheath is effectively sharply pointed at its front end. Rear surface 420 is disposed at an angle substantially perpendicular to the longitudinal axis of sheath 405. Sheath 405 has an axial bore 425 extending between its front surface 415 and its rear surface 420, and a straight slot 430 extending rearwardly from the sheath's front surface 415. Slot 430 terminates in a rear edge surface 435. Sheath 405 also includes a rigid finger grip 440 which extends radially outward from the sheath near its rear surface 420, and a stop 445 which extends radially outward from the sheath near its front end surface 415. Plunger 410 includes a body section 450 and a head section 455. Body section 450 and head section 455 are formed integrally with one another. Body section 450 has a circular cross-section and terminates in a front surface 460. Plunger 410 is sized so that body section 450 makes a close sliding fit within bore 425 of sheath 405, and so that its leading tip 460 will protrude from the front end of the sheath a short distance when the plunger's head section 455 is in engagement with the sheath's rear surface 420 (see FIG. 13).

Similarly, sheath 406 is a cylindrical tube that terminates in a flat annular surface 416 at its front end and a flat surface 421 at its rear end. Front surface 416 is disposed at an inclined angle (approximately 30 degrees) relative to the longitudinal axis of sheath 406, so that the sheath is effectively sharply pointed at its front end. Rear surface 421 is disposed at an angle substantially perpendicular to the longitudinal axis of sheath 406. Sheath 406 has an axial bore 426 extending between its front surface 416 and its rear surface 421, and a straight slot 431 extending rearwardly from the sheath's front surface 416. Slot 431 terminates in a rear edge surface 436. Sheath 406 also includes a rigid finger grip 441 which extends radially outward from the sheath near its rear surface 421, and a stop 446 which extends radially outward from the sheath near its front end surface 416. Plunger 411 includes a body section 451 and a head section 456. Body section 451 and head section 456 are formed integrally with one another. Body section 451 has a circular cross-section and terminates in a front surface 461. Plunger 411 is sized so that body section 451 makes a close sliding fit within bore 426 of sheath 406, and so that its leading tip 461 will protrude from the front end of the sheath a short distance when the plunger's head section 456 is in engagement with the sheath's rear surface 421 (see FIG. 13).

Sheaths 405 and 406 are attached to one another to form a unitary tool. Such attachment may be achieved in any number of ways well known to one skilled in the art, but preferably this attachment is achieved by a rigid cross member 443 attached to both sheaths, with or without the use of additional support members. Sheaths 405 and 406 are attached together so that their front tips are aligned with one another, as are their rear surfaces 420 and 421, their slots 430 and 431, and their stops 445 and 446.

Tool 400 is adapted to receive a fastener 305 in the manner shown in FIG. 11, i.e., the bar-like head 315 of the fastener is positioned inside bore 425 of sheath 405, end surface 325 leading and end surface 330 trailing, and the bar-like head 316 of the fastener is positioned inside bore 426 of sheath 406, end surface 326 leading and end surface 331 trailing, while filament 310 extends out through slots 430 and 431. Fastener 305 and tool 400 are carefully sized relative to one another so that heads 315 and 316 make a relatively close sliding fit within sheaths 405 and 406, respectively, whereby the fastener may be easily loaded into the sheaths but is capable of only minimal random movement within the sheaths. It is to be appreciated that the width of each of slots 430 and 431 is larger than the diameter of filament 310 but smaller than the diameter of heads 315 and 316, in order to allow the filament to move lengthwise of the slots and to prevent heads 315 and 316 from leaving bores 425 and 426 through slots 430 and 431, respectively.

Figure 12:
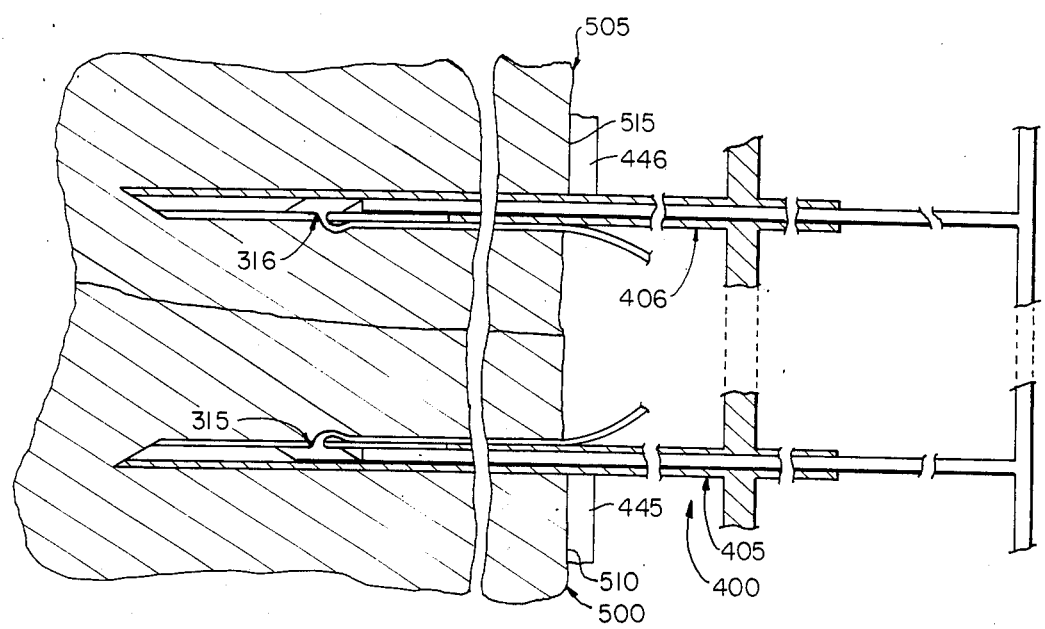
FIGS. 12-14 are sectional views in side elevation illustrating the tool of FIG. 11 deploying the surgical fastener of FIG. 10 in body tissue.

Once fastener 305 has been loaded in tool 400 in the foregoing manner, tool 400 is ready to implant the fastener. Looking next at FIG. 12, the fastener is deployed by advancing tool 400 so that its pointed tips will pierce adjoining pieces of body tissue 500 and 505, sheath 405 passing into tissue member 500 and sheath 406 passing into tissue member 505, until stops 445 and 446 engage the outer surfaces 510 and 515 of tissue members 500 and 505, respectively. Plungers 410 and 411 are retained in retracted position as the sheaths are inserted into the two tissue sections. Heads 315 and 316 of fastener 305 are carried inside the body tissue by the front tips of the tool, while filament 310 of the fastener is bent through interaction with surrounding tissue so as to extend substantially adjacent and parallel to sheaths 405 and 406, with the middle section of the filament residing outside the tissue. It is to be appreciated that stops 445 and 446 are carefully positioned relative to sheaths 405 and 406 so as to properly regulate the depth of penetration of the tissue by tool 400.

Figure 13:
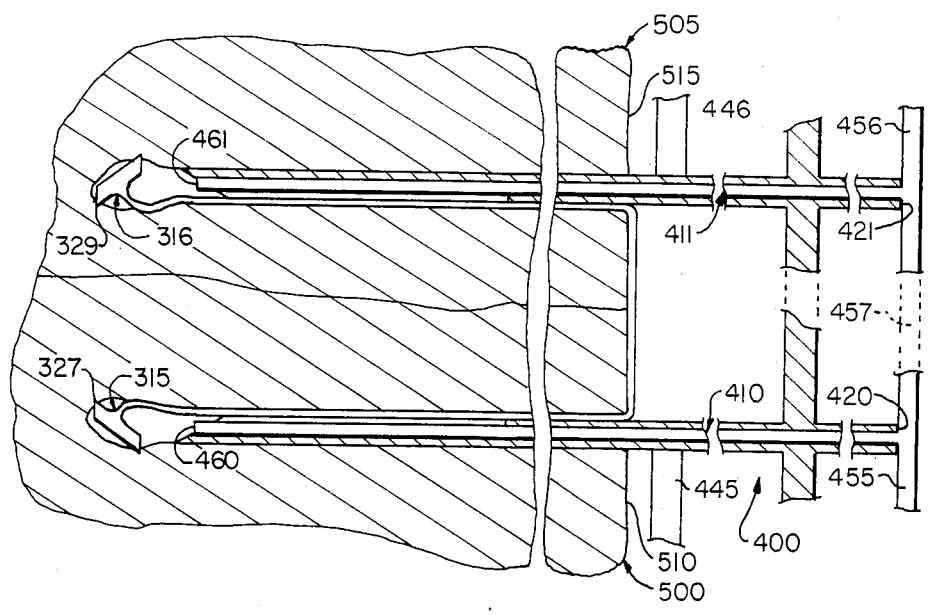

Looking next at FIG. 13, the heads of the fastener are thereafter ejected from the tool and deployed into the body tissue by pushing plungers 410 and 411 forward (preferably the heads 455 and 456 of plungers 410 and 411 are joined to one another by a rigid connecting member 457 so as to coordinate their movement relative to one another) until head sections 455 and 456 engage the rear surfaces 420 and 421 of the sheaths. As this occurs, the leading ends 460 and 461 of the plungers engage the rearmost portions of the fastener heads and force them forward, thereby propelling the fasteners out of the sheath and into the tissue. Tool 400 typically retreats slightly under this action, leaving openings in the tissue to accomodate the fastener's heads. The resilient nature of the fastener thereupon causes the fastener to try to straighten on itself in the manner of fastener 5 described above, whereby the sharply pointed ends 327 and 329 of the fastener's heads 315 and 316 will dig into the surrounding tissue as the heads attempt to resume their normal position substantially perpendicular to the adjoining filament 310.

Due to the fact that the holes formed in the tissue by the retreating tool 400 are significantly smaller in diameter than the length of fastener heads 315 and 316, (i.e., the distance between angled surfaces 325 and 330 and angled surfaces 326 and 331), and also to the fact that those holes will tend to close inwardly under the pressure of the surrounding resilient tissue, the heads 315 and 316 will typically be able to return only a fraction of the way back to their original perpendicular position; however, the sharply pointed ends of the fastener's heads will nonetheless penetrate into the surrounding tissue sufficiently to anchor the fastener to the body tissue. It is to be appreciated that as heads 315 and 316 attempt to return to their normal perpendicular positions, head 315 will rotate in a clockwise direction and head 316 will rotate in a counterclockwise direction, when viewed as in FIG. 13. It is believed obvious that by properly positioning the location of stops 445 and 446 on sheaths 405 and 406, the fastener can be set so that the filament 310 is drawn under tension against tissue surfaces 510 and 515 when the fastener is set.

Figure 14:
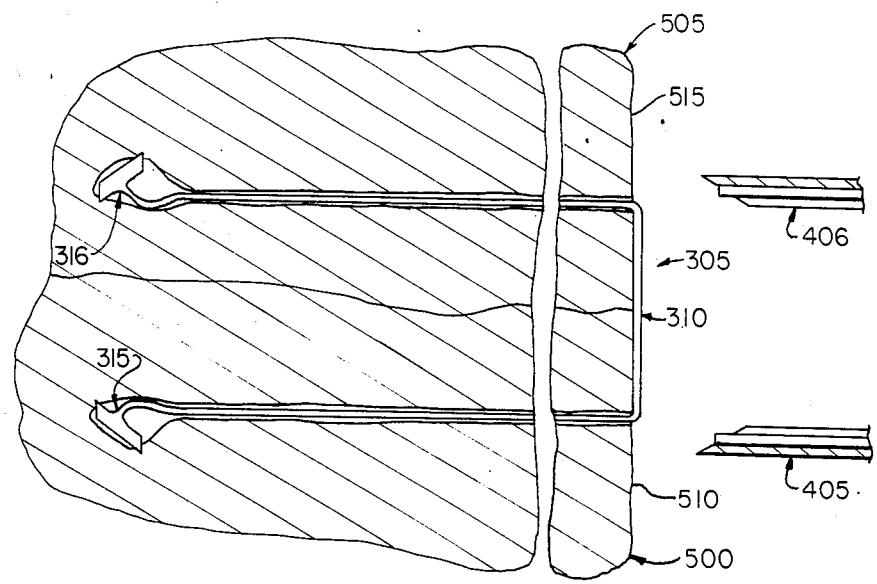

Thereafter, tool 400 is withdrawn from tissues 500 and 505 by pulling it backward, leaving the fastener set in the staple-like manner shown in FIG. 14 whereby its heads 315 and 316 are firmly emplanted in body tissues 500 and 505, respectively, and its filament 310 streches across and connects the two pieces of body tissue to one another. Fastener 305 will not easily come free from this position due to the holding action provided by heads 315 and 316. Indeed, on account of the angle at which the fastener's sharpened heads are disposed in the tissue, pulling on the exposed portion of filament 310 or efforts to separate the two pieces of tissue from one another tends to set the fastener's heads ever deeper into the tissue.

Figure 15:
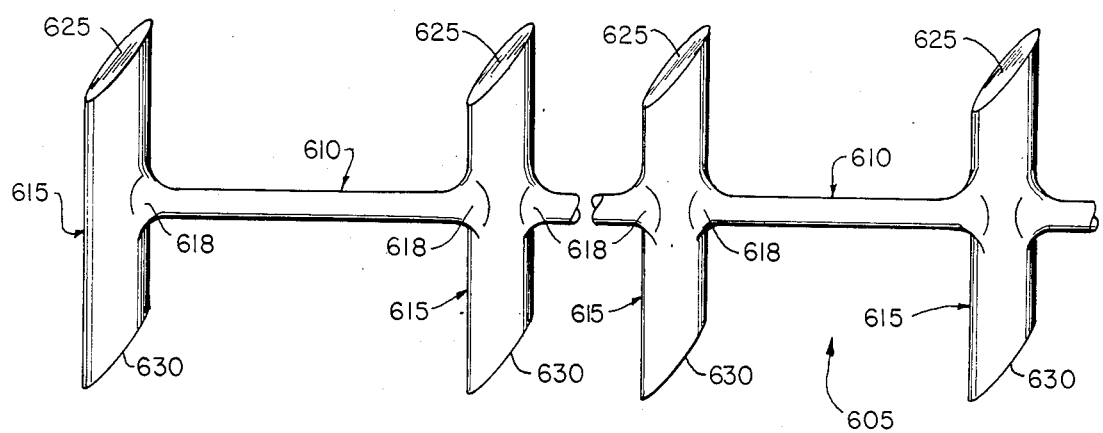
FIG. 15 is a perspective view illustrating a fifth form of surgical fastener made in accordance with the present invention.

Looking next at FIG. 15, there is shown a surgical fastener 605 which comprises a relatively long thin filament 610 having a plurality of identical relatively short, thick bar-like heads 615 disposed thereon. As shown at 618, filament 610 necks outward where it joins heads 615. Heads 615 are formed integral with filament 610 so that they normally extend at a right angle to the adjoining lengths of the filament. One end of each bar-like head 615 terminates in a flat surface 625, and the other end terminates in a flat surface 630. Surfaces 625 and 630 are set at an inclined angle (approximately 30-45 degrees) relative to the longitudinal axis of each head 615, whereby heads 615 are effectively sharply pointed at each end. It is to be appreciated that each of the surfaces 625 is pitched in the same direction as every other surface 625, and each of the surfaces 630 is pitched in the same direction as every other surface 630.

As with fasteners 5, 5A, 5B and 305 previously described, fastener 605 is formed out of a resilient material, with its relatively thin filament 610 being relatively flexible along its length and its relatively thick bar-like heads 615 being relatively stiff along their lengths. Fastener 605 may be of either a material that is absorbable by a living human body, or a material that is nonabsorbable by a living human body. While the precise dimensions of fastener 5 will vary according to the specific surgical application, fastener 605 may be sized so that filament 610 has a diameter of 0.015 inches, and heads 615 have diameters of 0.030 inches and lengths of 0.180 inches.

Figure 16:
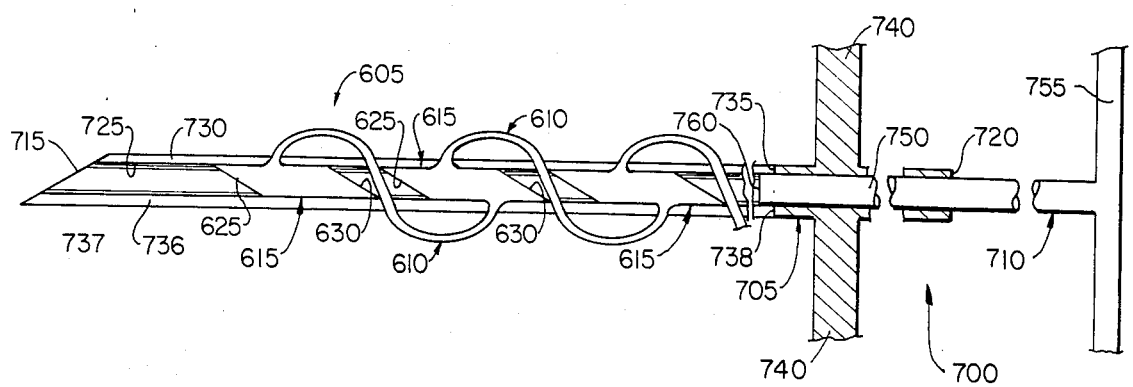
FIG. 16 is a longitudinal sectional view of a tool for deploying the surgical fastener shown in FIG. 15.

Looking next at FIG. 16, there is shown a tool 700 for deploying a fastener 605. Tool 700 is very similar to tool 100 previously described, except for a number of features hereinafter described. More particularly, tool 700 generally comprises a tubular sheath or needle 705 and a plunger or ram 710. Sheath 705 terminates in a flat annular surface 715 at its front end and a flat surface 720 at its rear end. Front surface 715 is disposed at an inclined angle (approximately 30 degrees) relative to the longitudinal axis of sheath 705, so that the sheath is effectively sharply pointed at its front end. Rear surface 720 is disposed at a right angle to the longitudinal axis of sheath 705. Sheath 705 has an axial bore 725 extending between its front surface 715 and its rear surface 720 and two diametrically aligned slots 730 and 736 that intersect the axial bore. Slot 730 extends rearward from the sheath's front surface 715 and terminates in a rear surface 735. Slot 736 extends rearward from a front surface 737 and terminates in a rear surface 738. Sheath 705 also includes a pair of diametrically aligned, radially extending finger grips 740. Plunger 710 includes a body section 750 and a head section 755. Body section 750 and head section 755 form a one-piece unit. Body section 750 terminates in a front surface 760. Plunger 710 is sized so that body section 750 makes a close sliding fit in bore 725 of sheath 705. Plunger 710 has a length such that its leading surface 760 will protrude from the front end of the sheath when the plunger's head section 755 is engaged with the sheath's rear end surface 720.

Tool 700 receives a fastener 605 in the manner shown in FIG. 16, i.e., the bar-like heads 615 of the fastener are positioned inside bore 725 of sheath 705, end surfaces 625 leading and end surfaces 630 trailing, while the portions of filament 610 that connect heads 615 extend in and out of slots 730 and 736 and between the heads of the fasteners. Fastener 605 and tool 700 are carefully sized relative to one another so that heads 615 make a sliding fit within the sheath, whereby heads 615 may be easily loaded into the sheath, but are permitted only minimal lateral or pivotal movement within the sheath. Slots 730 and 736 are sized so as to have a width that is greater than the diameter of filament 610 but smaller than the diameter of heads 615, so that the filament but not the heads may extend through the slots.

Figure 17:
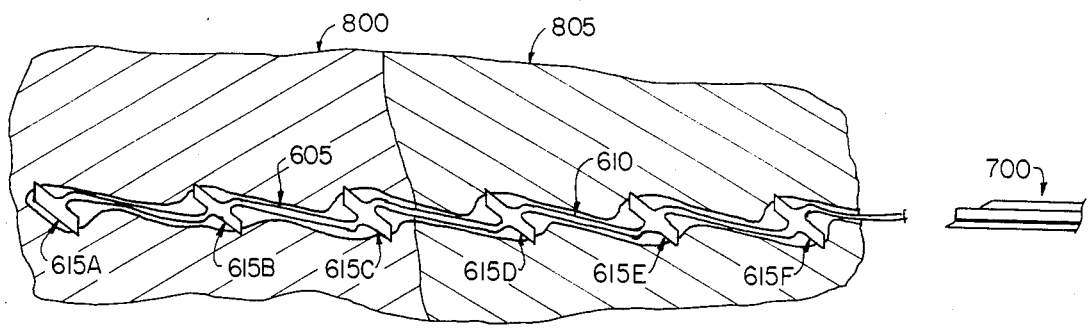
FIG. 17 is a sectional view in side elevation illustrating the surgical fastener of FIG. 15 attaching two different pieces of body tissue to one another.

The fastener is deployed by plunging tool 700 pointed tip first into two adjoining body tissues. As this occurs, the heads 615 of the fasteners are carried inside the body tissues by the front tip of the tool, while the portions of filament 610 that extend through slots 730 and 736 are bent through interaction with the surrounding tissue so as to lie nearly flat against sheath 705. Referring now to FIG. 17, the fastener is thereafter set into the tissue by pressing plunger 710 forward until the fastener head 615A closest to front tip 715 is propelled out of the sheath and into the tissue. Tool 700 typically retreats slightly under this action, leaving an opening in the tissue to accomodate the fastener's head. The resilient nature of the fastener thereupon urges the fastener to straighten on itself, whereby the sharply pointed ends of head 615A will dig into the surrounding tissue as the head attempts to return to its normal position substantially perpendicular to the adjoining length of filament. Due to the fact that the hole formed in the tissue by the retreating tool 700 is significantly smaller in diameter than the length of the fastener's head, and due also to the fact that the hole will tend to close inwardly somewhat under the pressure of the surrounding resilient tissue, head 615A will typically be able to return only a fraction of the way back to its original perpendicular position; however, the sharply pointed ends of head 615A will allow the fastener to penetrate sufficiently into the walls of the tissue so that the fastener's head will be anchored to the body tissue.

Thereafter tool 700 is retreated slightly and the foregoing operation repeated so as to set the next head 615B of the fastener into the tissue. Then the tool is retreated once more and the next head 615C of the fastener is set, in the same manner as heads 615A and 615B. The foregoing operation is repeated until the fastener has been fully deployed into the tissue and the tool withdrawn. In FIG. 17 the deployed fastener has six heads 615A-615F, all set in the same manner. The engagement of the pointed tops of heads 615A-615F with the surrounding tissue assures that fastener 605 is firmly emplanted in body tissues 800 and 805, whereby they are secured together. Fastener 605 will not easily come free from this position due to the holding action provided by the multiple heads 615. Indeed, on account of the fact that the fastener's multiple heads are each barbed on their two opposite ends, the single fastener 605 is able to provide bi-directional restraint whereby the two separate tissue members are held in tight contact with one another. In fact, on account of the angle at which the fastener's sharpened heads are disposed in the tissue, efforts to separate the tissue members 800 and 805 from one another tends to set the heads of the fastener even deeper into the tissue.

MODIFICATIONS OF THE PREFERRED EMBODIMENT

It is to be appreciated that the preferred embodiment of the invention may be modified in a number of ways without departing from the scope of the present invention.

Thus, for example, the head 15 and filament 10 of fastener 5 need not be formed integrally with one another, but instead they may be pre-formed as separate elements and later attached to one another so as to form an integral unit. Additionally, head 15 could be formed out of a different material than filament 10, e.g. head 15 may be formed out of material having a much higher durometer value than filament 10. Furthermore, although the head and filament of the fasteners shown in the drawings have a circular cross-section, it is contemplated that they may have a different cross-sectional shape, e.g., triangular, elliptical, hexagonal, etc.

These and other changes of their type will be obvious to a person skilled in the art, and are believed to be within the scope of the present invention.

ADVANTAGES OF THE INVENTION

Numerous advantages are obtained by using the present invention.

First, the present invention provides an improved surgical fastener of the T-bar variety, wherein when at least one end thereof is anchored inside body tissue, that end of the fastener will remain solidly anchored in the tissue despite the application of a substantial pulling force.

Second, the present invention provides an improved surgical fastener of the T-bar variety which is simple and inexpensive to make, and easy to use.

Third, the present invention provides an improved surgical fastener of the T-bar type which can be made either absorbable or non-absorbable to the human body.

What is claimed is:

1. An improved surgical fastener comprising:
   a resilient filament that is relatively flexible along its length, and at least one elongated head that is relatively inflexible along its length;
   said at least one elongated head being attached to said filament so that said filament normally is substantially perpendicular to said at least one elongated head;
   characterized in that at least one end of said elongated head is sharply pointed;
   whereby when said at least one elongated head is driven lengthwise into tissue with said filament bent relative to said elongated head so as to extend substantially parallel to the driving axis, the resiliency of said filament will (a) cause said elongated head to tend to turn to restore the original perpendicular position of said filament relative to said at least one elongated head and (b) cause said at least one sharply pointed end of said at least one elongated head to embed itself further into said tissue, thereby securely anchoring said fastener in said tissue so that it may not be easily withdrawn by pulling on said filament.

2. A surgical fastener according to claim 1 wherein at least one end of said at least one elongated head is bevelled to form a sharp point.

3. A surgical fastener according to claim 2 wherein said sharp point is eccentric of the longitudinal axis of said at least one elongated head.

4. A surgical fastener according to claim 1 wherein both ends of said at least one elongated head are sharply pointed.

5. A surgical fastener according to claim 4 wherein both ends of said at least one elongated head are bevelled to form sharp points.

6. A surgical fastener according to claim 5 wherein both of said sharp points are eccentric of the longitudinal axis of said at least one elongated head.

7. A surgical fastener according to claim 6 wherein said sharp points are disposed on opposite sides of said longitudinal axis of said at least one elongated head.

8. A surgical fastener according to claim 1 having at least three of said elongated heads connected by portions of said filament.

9. A surgical fastener according to claim 1 wherein said fastener is made of a synthetic polymerized resin.

10. A surgical fastener according to claim 1 wherein said fastener is made of a material that is absorbable by living human or animal tissue.

11. A surgical fastener according to claim 1 wherein said fastener is made of a material that is not absorbable by living human or animal tissue.

12. A surgical fastener according to claim 1 wherein said filament has an outer diameter of about 0.015 inches, said at least one elongated head has an outer diameter of about 0.030 inches, and said at least one elongated head has a length of about 0.18 inches.

13. A surgical fastener according to claim 1 wherein said fastener is formed out of a polylactide copolymer or a glycolide copolymer or a nylon, or a polyethylene or a carbonate polymer or a polyether ester copolymer.

14. A surgical fastener according to claim 1 wherein said at least one elongated head is pointed eccentrically of the longitudinal axis of said at least one head.

15. A surgical fastener according to claim 1 wherein said filament has at least one rib thereon to engage a washer.

16. A surgical fastener according to claim 15 wherein said at least one rib is conically shaped.

17. A surgical fastener according to claim 1 having a pair of said elongated heads, and further wherein said elongated heads are disposed at opposite ends of said filament.

18. A surgical fastener according to claim 17 wherein at least one end of each of said pair of elongated heads is bevelled to form a sharp point.

19. A surgical fastener according to claim 17 wherein both ends of each of said pair of elongated heads are sharply pointed.

20. A surgical fastener according to claim 19 wherein both ends of each of said pair of elongated heads are bevelled to form sharp points.

21. A surgical fastener comprising:

a resilient filament that is relatively flexible along its length; and at least one elongated head that is relatively inflexible along its length;

said at least one elongated head being attached to said filament so that when said fastener is unstressed said filament is substantially perpendicular to said at least one elongated head; and at least one end of said elongated head being sharply pointed;

whereby when said at least one elongated head is driven lengthwise into tissue while said filament is bent adjacent said at least one elongated head so that at least a portion thereof extends substantially parallel to said at least one elongated head, the resiliency of said filament will cause said elongated head to tend to turn to restore the original perpendicular position of said filament relative to said at least one elongated head, so that said at least one sharply pointed end of said at least one elongated head will embed itself further into said tissue, whereupon said fastener will be securely anchored in said tissue and may not be easily withdrawn by pulling on said filament.

22. A surgical fastener according to claim 21 wherein said filament has at least one rib thereon to engage a washer.

23. A surgical fastener according to claim 22 wherein said at least one rib is conically shaped.

24. A surgical fastener according to claim 21 wherein said at least one end of said at least one elongated head is bevelled to form a sharp point at said at least one end.

25. A surgical fastener according to claim 24 wherein said sharp point is eccentric of the longitudinal axis of said at least one elongated head.

26. A surgical fastener according to claim 21 wherein said at least one elongated head is pointed eccentrically of the longitudinal axis of said at least one elongated head.

27. A surgical fastener according to claim 21 having at least three heads connected by portions of said filaments.

28. A surgical fastener according to claim 21 wherein said filament has an outer diameter of about 0.015 inches, said at least one elongated head has an outer diameter of about 0.030 inches, and said at least one elongated head has a length of about 0.18 inches.

29. A surgical fastener according to claim 21 wherein said fastener is formed out of a polylactide copolymer or a glycolide copolymer or a nylon or a polyethylene or a carbonate polymer or a polyether ester copolymer.

30. A surgical fastener according to claim 21 having two elongated heads connected by said filament.

31. A surgical fastener according to claim 30 wherein at least one end of each of said pair of elongated heads is bevelled to form a sharp point.

32. A surgical fastener according to claim 30 wherein both ends of each of said pair of elongated heads are sharply pointed.

33. A surgical fastener according to claim 32 wherein both ends of each of said pair of elongated heads are bevelled to form sharp points.

34. A surgical fastener according to claim 21 wherein both ends of said at least one elongated head are sharply pointed.

35. A surgical fastener according to claim 34 wherein both ends of said at least one elongated head are bevelled to form sharp points.

36. A surgical fastener according to claim 35 wherein both of said sharp points are eccentric of the longitudinal axis of said at least one elongated head.

37. A surgical fastener according to claim 36 wherein said sharp points are disposed on opposite sides of said longitudinal axis of said at least one elongated head.

* * * * *